United States Patent
Exalto et al.

(10) Patent No.: US 9,034,300 B2
(45) Date of Patent: May 19, 2015

(54) COMPOSITION AND METHOD FOR MEDICAL IMAGING OF BODY CAVITIES

(75) Inventors: Niek Exalto, Rotterdam (NL); Mark Hans Emanuel, Aerdenhout (NL)

(73) Assignee: Giskit B.V., Delft (NL)

(*) Notice: Subject to any disclaimer, the term of this patent is extended or adjusted under 35 U.S.C. 154(b) by 0 days.

(21) Appl. No.: 13/502,232

(22) PCT Filed: Oct. 15, 2010

(86) PCT No.: PCT/NL2010/050679
§ 371 (c)(1),
(2), (4) Date: May 25, 2012

(87) PCT Pub. No.: WO2011/046437
PCT Pub. Date: Apr. 21, 2011

(65) Prior Publication Data
US 2012/0230915 A1    Sep. 13, 2012

(30) Foreign Application Priority Data

Oct. 16, 2009  (NL) ..................................... 2003660

(51) Int. Cl.
*A61B 8/00*        (2006.01)
*A61K 49/22*       (2006.01)

(52) U.S. Cl.
CPC .................................. *A61K 49/222* (2013.01)

(58) Field of Classification Search
USPC ....................................................... 424/9.52
See application file for complete search history.

(56) References Cited

U.S. PATENT DOCUMENTS

| 4,310,510 | A | * | 1/1982 | Sherman et al. ................. 424/45 |
| 4,680,175 | A |   | 7/1987 | Estis et al. |
| 4,681,119 | A |   | 7/1987 | Rasor et al. |
| 4,985,233 | A |   | 1/1991 | Klaveness et al. |
| 5,352,434 | A |   | 10/1994 | Illig et al. |
| 5,425,366 | A | * | 6/1995 | Reinhardt et al. ............. 600/458 |
| 6,231,513 | B1 | * | 5/2001 | Daum et al. ................... 600/458 |
| 6,280,702 | B1 |   | 8/2001 | Carter et al. |
| 7,727,155 | B2 |   | 6/2010 | De Ziegler |
| 2003/0206862 | A1 |   | 11/2003 | Gieselmann |
| 2005/0255039 | A1 |   | 11/2005 | Desai |
| 2008/0206161 | A1 |   | 8/2008 | Tamarkin et al. |

FOREIGN PATENT DOCUMENTS

| EP | 1 793 860 B1 | 6/2007 |
| EP | 1793660 A1 | 6/2007 |

(Continued)

OTHER PUBLICATIONS

Killick (J R Soc Med 1999;92:628-631).*

(Continued)

*Primary Examiner* — Benjamin Packard
(74) *Attorney, Agent, or Firm* — Gilberto M. Villacorta; Sunit Talapatra; Foley & Lardner LLP

(57) ABSTRACT

A foamed aqueous image enhancing composition containing cellulose and/or cellulose derivative(s), has a pH between 5.5 and 7, wherein the viscosity of the composition is less than 1800 mPa·sec, and wherein a gas is maintained in the composition for at least 1 minute after preparation. The combination of low viscosity and foam stability makes the composition particularly suitable in patency tests and fallopian tube sterilization checks.

8 Claims, 1 Drawing Sheet

(56) References Cited

FOREIGN PATENT DOCUMENTS

| EP | 1793860 B1 | 8/2009 |
| WO | WO-92/00707 | 1/1992 |
| WO | WO 94/07417 | 4/1994 |
| WO | 01/24775 A1 | 4/2001 |
| WO | 01/82937 A1 | 11/2001 |
| WO | 03/094710 A2 | 11/2003 |
| WO | WO-03/094710 | 11/2003 |
| WO | 2004/073750 A1 | 9/2004 |
| WO | 2006/006861 A1 | 1/2006 |
| WO | 2007/030002 A1 | 3/2007 |

OTHER PUBLICATIONS

Boudghène (Ultrasound Obstet Gynecol 2001; 18: 525-530).*
International Search Report, dated Feb. 11, 2011, from corresponding PCT application.
Chi-Fishman, et al. "Effects of Systemantic Bolus Viscosity and Volume Changes on Hyoid Movement Kinematics", Dysphagia (2002), pp. 1-17.
MSDS—Methyl—cellulose (2% solution in water) viscosity 3500-5600—ACC# 00966 (1998) 5 pgs.

* cited by examiner

COMPOSITION AND METHOD FOR MEDICAL IMAGING OF BODY CAVITIES

FIELD OF THE INVENTION

This invention relates to compositions and methods for medical imaging of the human or animal body, in particular to medical imaging with high contrast. More in particular, it pertains to image enhancing agents suitable in a patency test or in verifying fallopian tube sterilization.

BACKGROUND OF THE INVENTION

Medical diagnostic imaging is widely used for the examination of body cavities. A prerequisite for the imaging of body cavities is the instillation of a fluid in order to obtain a fluid-filled cavity. In these fluid-filled cavities, the fluid has two functions: (1) to open up the cavity from its "collapsed" state (distension) and (2) to enhance the contrast of the image of the body cavity. Conventionally, water or watery fluids are used for distension and contrast imaging. In intervention cardiology or radiology, kidneys, liver, intestines, this is sometimes combined with the generation of bubbles, to further increase contrast in the veins. Examples of so-called microbubbles are given by U.S. Pat. No. 4,681,119. Disadvantageously, the gas contained in these watery fluids disappears almost instantaneously, and would thus require continuous replenishment during imaging. However, this is often not very convenient for the patient.

On the other hand, EP 1,793,860 provides a solution to overcome the inconveniences and discomfort caused by leakage of aqueous solutions while imaging. Thereto, it discloses a gel composition having a viscosity of between 2000 and 4000 mPa·sec, containing cellulose or cellulose derivative. The composition may be used for the imaging of any body cavity. The commercially available ExEm® falls within the scope of EP 1,793,860. The gel is stable and does not contain any particles or micro bubbles. In fact, these are considered to give rise to artifacts. Where excellent results are reported for the ExEm® e.g. when imaging the content of the uterine cavity, the composition appears not particularly suited when performing a patency test, i.e. to examine the fallopian tubes for blockage, either desired or undesired. It requires considerable pressure (causing pain to the patient) to insert the gel into the tubes, and even then it appears not feasible. In that respect, it is noted that it is of the essence that any difficulties experienced by inserting distenting media into the tubes should not be mistaken for real (permanent) blockage of the fallopian tubes.

Previously, an ultrasound contrast agent ECHOVIST was marketed by Schering AG, which agent consisted of a suspension of micron-sized air bubbles, formed upon reconstitution of specially formulated galactose granules with an aqueous galactose solution. Amongst other drawbacks, its ingredients and tedious preparation made it a costly tool to visualize the fallopian tubes. It appears no longer available on the market.

Outside the field of the invention, US 2003/0206862 describes a contrast medium for intraveous administration, wherein small gas bubbles are introduced into the bloodstream. The ultrasound contast medium contains solid polyoxyethylene-660-12-hydroxystearate particles. It goes without saying that the intravenous applications taught in US 2003/0206862 put less constraints to the use of solid particles, while the skilled person in the field of sterilization and fertility investigations is searching for particle-free, embryotoxic-free solutions. Adhesion is to be prevented at all cost.

There is thus a need in the art for a simplified, cost-effective agent for imaging of fallopian tubes which is easy-to-handle, enables high quality images without jeopardising the health of the patient and without loss of echogenicity during imaging.

SUMMARY OF THE INVENTION

In view of the above objectives, it has been found that filling of the fallopian tubes and associated visualization while imaging can be improved when foaming an image enhancing composition such as that according to EP1793660 prior to imaging. Where the air bubbles improved visualisation, the decreased viscosity enables the medical examiner to insert the composition without excessive force, even through the small fallopian tubes. The composition is sufficiently viscous to provide a stable distribution of gas bubbles during examination, while at the same time its viscosity is low enough to assure that it could be inserted into the fallopian tubes, without excessive force and associated pain for the patient. Hence, the composition does not interfere with the diagnosis whether the fallopian tubes are open or closed. After all, when diagnosing "blockage", the medical practitioner must be certain that the composition could have accessed the tubes if it were not for the blockage. At the conditions given here below, it was found that the composition according to the invention can hold the air pockets for a time sufficiently long to perform imaging without loss of echogenicity, and without the need for replenishment.

The composition is free from particulate material and particularly suited for evaluation of tubal patency in infertility investigations, and as a control on fallopian tube sterilization. Also, fertility enhancing effects have been ascribed to the composition according to EP1793660, which—without wishing to be bound to any theory—are associated with the lubricating effect of the composition.

The foamed image enhancing composition has also been found convenient when imaging body cavities other than the fallopian tubes, scanning for abnormalities, particularly when determining the shape and/or size of body cavities. The foamed composition provides great contrast and easy access to all parts of the cavities, thus yielding a sharp contrast between the cavity and its walls. The uterus is specifically preferred.

DETAILED DESCRIPTION

Figure 1:
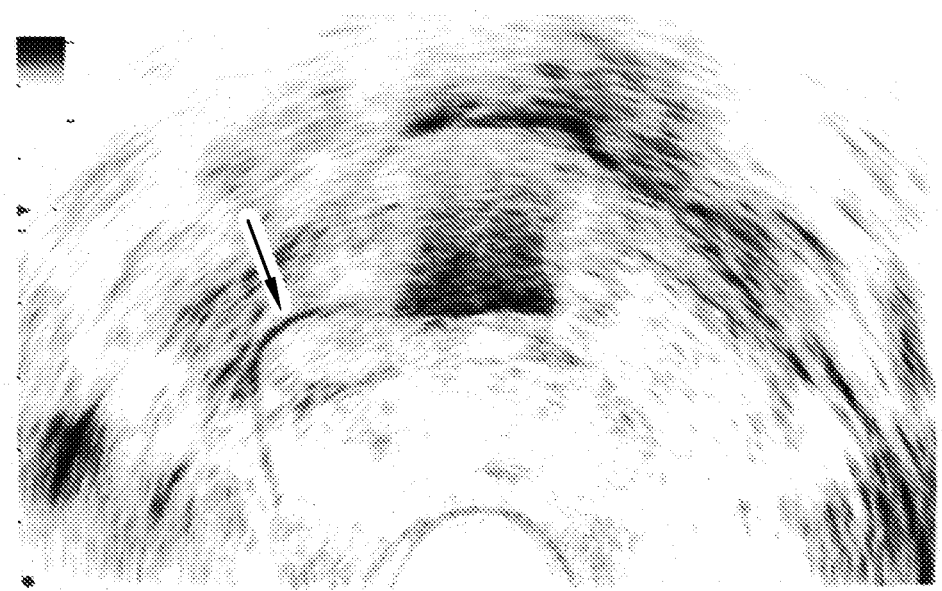
FIGS. 1 and 2 show images showing fallopian tubes completely filled with the foamed composition according to the invention. For enhanced contrast in the application, the negatives corresponding to the original images are presented.

In one aspect, the present invention relates to a foamed aqueous image enhancing composition containing cellulose and/or cellulose derivative(s), for improved imaging of a body cavity, particularly the fallopian tubes, wherein the viscosity of the composition is less than 1800 mPa·sec, as determined by standard viscosity determination methods, measured at room temperature and under atmospheric pressure. Unless mentioned otherwise, the viscosity numbers in the context of the invention are the dynamic viscosities determined using a Brookfield rotational viscometer, at room temperature (i.e. 25° C.). With "foamed" it is understood that the gas inserted into the composition is maintained within the composition for at least 1 minute, more preferably at least 2 minutes, more preferably at least 5 minutes, most preferably at least 10 minutes, after preparation. All this time, the gas bubbles introduced mechanically will be maintained in the composition. Although not considered detrimental to the invention, foam stability over time periods extending beyond 20 minutes are not preferred. Over the above time periods, the foam is considered stable. To keep it simple and cost-effective, it is preferred that the gas is or comprises ambient air. The composition is non-embroyotoxic.

Cellulose derivatives comprise cellulose ethers preferably selected from alkyl celluloses, hydroxyalkyl celluloses and hydroxyalkyl alkyl celluloses. Examples of suitable cellulose ethers are methylcellulose (MC), ethylcellulose (EC), hydroxyethyl cellulose (HEC), hydroxypropyl cellulose (HPC), hydroxypropyl methylcellulose (HPMC), hydroxypropyl ethylcellulose (HPEC), ethylhydroxyethylcellulose (EHEC), hydroxyethyl methylcellulose (HEMC), and the like. Hydroxyethylcellulose is most preferred.

The pH value of the composition is buffered in the range between about 5.5 and about 7.5. Preferably, between about pH 6.0 and about 7.0, more preferably between about pH 6.3 and about 6.8.

The viscosity of the foamed composition is preferably less than 1500 mPa·s, more preferably less than 1000 mPa·s, most preferably less than 800 mPa·s, particularly less than 500 mPa·s. The actual viscosity may be readily set by the medical examiner when preparing the foam, depending on the application: Lower viscosities are particularly preferred when examining the fallopian tubes after fallopian tube sterilization surgery. At lower viscosities, the risk of pressure build-up, pain and potential damage to the tubes is avoided. The lower viscosities may however necessitate catheters. It is preferred that the viscosity of the composition is more than 4, 5, 10, 15, 20, 30, 40, 50, 80, 100 mPas. This way leakage of image enhancing composition is minimized, and foam stability is guaranteed. The composition may be used in connection with catheters known in the art. Excellent results are obtained with the sealing stopper and assembly disclosed in WO2007/030002, herein incorporated by reference.

The skilled person will understand that adjuvants, such as disinfectants or a local anaesthetic, may be present in the composition, for instance lidocaine and chlorohexidine. It may be preferred to use such anaesthetics when examining after intratubal placement. In other embodiments the use of local anaesthetics is not preferred or even avoided. The composition preferably further contains one or more lubricants, preferably glycerine. If lubricants other than glycerine are employed, these should be non-embryotoxic (i.e. anything which can adversely affect the growth or development of the embryo). In addition contrast enhancers may be added, such as iodine for X-ray imaging. However, in a preferred embodiment of the invention the solid content of the gel consists substantially of a cellulose derivative, such as hydroxyethylcellulose or methylcellulose in a buffer, and glycerine. The composition of the invention consists of substances which are safe for use in the human or animal body. It should be echolucent and therefore not contain particulate material, such as starch. Suitably, the composition is clear and does not contain particles or protein. It is also considered non-embryotoxic.

The present invention also pertains to a method for preparing such a foamed composition by (i) providing an aqueous (gel) composition containing cellulose and/or cellulose derivative(s), having a viscosity ranging between 2000 and 4000 mPa·sec, and a pH between 5.5 and 7, and (ii) inserting air, alone or in combination with aqueous solution, into said composition (i.e. foaming), to produce a foamed composition containing air bubbles or pockets and having a viscosity decreased to acceptable levels. The "insertion" can be realized by all means that result in foaming, typically mechanically, by pumping. A suitable composition to be foamed is given by EP 1.793.860, its contents herein incorporated by reference. Here below, the highly viscous raw material is referred to as the gel composition, thus distinguishing from the foamed composition according to the invention.

The gel composition provided comprises cellulose or a cellulose derivative as described above. The amount of cellulose or cellulose derivative is to achieve a viscosity of between 2000 and 4000 mPa·sec., preferably between 2000 and 3000 mPa·sec. The composition thus exhibits gel-like behaviour. The cellulose (derivatives) play an important role in retaining the air bubbles. It is preferred that the gel composition contains between 1 and 5% cellulose (and/or derivatives).

The skilled person will understand that adjuvants, such as disinfectants or a local anaesthetic, may be added. The composition preferably contains non-embryotoxic lubricant(s), preferably at least glycerine. If glycerine is present, it preferably contributes in amounts between 1 and 10% based on the total gel composition. In addition contrast enhancers may be added, such as iodine for X-ray imaging. However, in a preferred embodiment of the invention the solid content of the gel consists substantially of a cellulose derivative, such as hydroxyethylcellulose or methylcellulose, in a buffer, and glycerine. A suitable gel composition is commercially available under the name of ExEm®.

The pH value is as described above, and—in view of the above—the composition consists of substances which are safe for use in the human or animal body. It should be echolucent and therefore not contain particulate material, such as starch.

Although there are no limitations regarding the ways to insert air pockets into the gel, this may conveniently be achieved by pumping air, and (demineralised or purified) water or saline salt solution, both considered included in the term "aqueous solution", into the gel composition. Conveniently, this may be performed by the practitioner or assistant in the presence of the patient immediately prior to imaging, preferably by connecting a first syringe, containing a predetermined amount of the gel composition, with a second syringe, filled with air or a predetermined amount of aqueous solution, and pumping the contents of the second syringe and the first syringe back and forth, until a suitable foam is formed. The syringes may be connected using simple (medical) tubing, optionally with a mixing chamber in between.

In one embodiment, foaming is realized by pumping air into the aqueous gel composition, i.e. no water added to the gel composition. This will result in foamed compositions having a viscosity at the higher end of the above range, and is found particularly useful when examining a body cavity for its shape. The bubbles are found to improve the image. In these cases, problems caused by administering the relatively viscous composition into the cavity are of less concern.

However, in a preferred embodiment, the gel composition is foamed using an aqueous solution and air, particularly where imaging concerns a patency test or a fallopian tube sterilization check. The relative amounts of the gel composition and the aqueous solution are selected such that the end viscosity is within the desired range. The desired viscosity may conveniently be assessed by the medical practitioner, and he may adjust the amount of aqueous solution mixed with the gel composition according to his or her needs. A syringe containing the (maximum allowable amount of) aqueous solution, said syringe having a calibrated scale, preferably even in combination with an instruction manual that helps to convert the numbers in terms of viscosities, may be of help. As a guide, the volume ratio aqueous solution:gel composition is preferably at least 1:99. More preferably, the relative volume ratio between the aqueous solution and the gel composition ranges between 10:90 and 90:10 (vol %), more preferably between 20:80 and 80:20, even more preferably between 30:70 and 70:30, more preferably between 40:60 and 60:40. The actual mixing ratio depends on the purpose of the examination; in case of patency test, significant amounts of water are preferred; excellent results are obtained at a 50:50 ratio (vol %). The above numbers on cellulose and optional glycerine content can readily be recalculated to the foamed and diluted composition.

The present invention also pertains to a kit of parts comprising (i) an aqueous image enhancing composition comprising cellulose or cellulose derivate, said composition having a viscosity ranging between 2000 and 4000 mPa·sec, as determined by standard viscosity determination methods, measured at room temperature and under atmospheric pressure; and (ii) an aqueous solution (purified or demineralised water or a saline solution). Both (i) and (ii) are preferably provided in a sealed and sterilized state, preferably in a syringe. A suitable composition (i) is commercially available by the name of ExEm®. Optionally the kit also comprises means for connecting both syringes to one another, e.g. a piece of medical tubing. The entire kit can be disposed of after preparing the foam and the treatment/examination has taken place. For sake of completeness, solution (ii) has a viscosity corresponding to that of water, and contains no viscosity increasing agents.

Conveniently, the syringes may be filled with the gel composition (i) and the aqueous composition (ii) in pre-determined amounts, to achieve a mixing ratio as described above. In one embodiment, the syringe (ii) contains the aqueous solution in an amount that corresponds with the maximum allowable amount to achieve a low-viscous stable foam. For instance, syringe (ii) contains an amount of aqueous solution with respect to syringe (i) containing the gel composition that corresponds to a volume ratio in the range of 80:20 to 99:1 (vol %), preferably around 90:10 (vol %).

In yet another aspect, the invention pertains to a method for imaging the (shape and/or size of) and/or diagnosing for abnormalities of a body cavity in a patient, said method comprising administering the above-described foamed image enhancing composition to the patient, and scanning the patient using imaging.

The image enhancing composition of the invention may be used for all types of medical imaging, including X ray imaging, echography, magnetic resonance imaging, CT scanning and ultrasound imaging. Preferably, they are used for ultrasound imaging. More preferably, it is used for 3-dimensional ultrasound imaging. In one embodiment, the compositions of the invention are used in 3-dimensional sonohysterography. As used herein, "image enhancement" refers to increasing the contrast of an image. The contrast enhancement may be either negative (black) or positive (white).

Typically, enhancement also involves distension of the body cavity of which an image is made. The compositions of the invention may be used for the imaging of any body cavity, including each part of the gastro-intestinal tract, such as the stomach, the colon, the duodenum; the bladder, the vagina. In a preferred embodiment, the body cavity is the uterine cavity. The foamed composition is found particularly useful in evaluating the size and shape of the cavity.

A medium comprising a composition of the invention may be administered or introduced in a body cavity by methods known in the art and depending on the body cavity which is to be examined. For instance, for examination of the uterus, the composition is typically administered via an instillation device, such as a catheter. The method comprises introducing the foamed composition in small aliquots in the body cavity. The skilled person will understand that the amount which has to be administered or introduced will be dependent on the size of the body cavity which has to be imaged. Typically, about 1-10 ml will be enough for most cavities. Constant infusion is not necessary.

In a preferred embodiment, the invention pertains to the use of the foamed image enhancing composition in a patency test, i.e. to determine whether the fallopian tubes are open or closed. The composition of the invention can be applied in a control on anti-conception methods known in the art, particularly in combination with Adiana®, Essure® and OvabLoc® intratubal devices. Typically such a test is performed within 3 to 6 months after fallopian tube sterilization surgery or intratubal placement.

In yet another aspect, the invention provides for high contrast images which are obtainable by using the compositions of the invention. Also encompassed in the invention, are high contrast 3-dimensional images. In particular, high contrast 3-dimensional images of the fallopian tubes. In a preferred embodiment, the invention is used for so-called virtual hysteroscopy. Three dimensional imaging requires a very stable and quiet filling of the cavity of interest, with a minimum amount of artefacts.

EXAMPLE

This example demonstrates how the compositions and method of the invention may effectively and safely be used for sonohysterography.

A syringe containing 10 ml of a sterile, clear viscous gel containing hydroxyethylcellulose, glycerine, buffered with acetic acid [Exem® (GIS-kit B.V.)] was connected to another syringe containing 10 ml demineralised water, using small plastic tubing. The water was now pumped into the other syringe, and back. This was repeated for 5 times, until a foam was produced. The dynamic viscosity as measured using Brookfield rotational viscometry at 25° C. was about 250 mPas.

Figure 2:
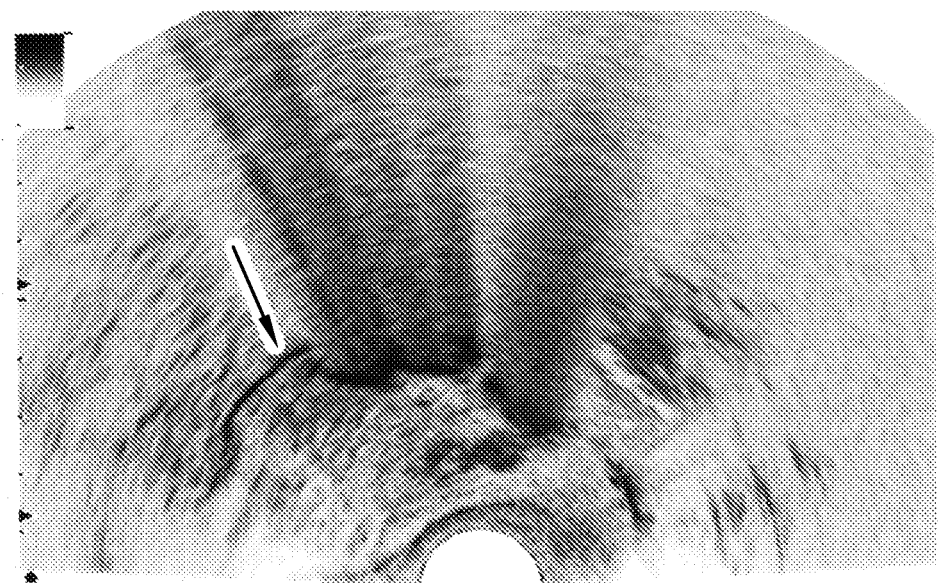

The foamed composition was now used for sonohysterography and introduced into the fallopian tubes using conventional ways. There was no excess force and the patients experienced no pain. The foam was stable during imaging. A clear image of the fallopian tubes could thus be provided, see FIGS. 1 and 2.

The invention claimed is:

1. A method for enhancing contrast of an image of a body cavity, comprising:
   (a) introducing a foamed aqueous image enhancing composition into a body cavity selected from uterus or fallopian tubes of a patient,
   said composition comprising cellulose and/or a cellulose derivative, having a pH between 5.5 and 7, and having a viscosity of less than 1800 mPa·sec, as determined by standard viscosity determination methods, measured at room temperature and under atmospheric pressure, and
   (b) scanning the patient using imaging technology,
   wherein a gas is maintained in the composition for at least 1 minute after initiating foaming.

2. The method according to claim 1, wherein said body cavity is the fallopian tubes.

3. The method according to claim 1, wherein said method is used in a patency test or in a check on fallopian tube sterilization surgery.

4. The method according to claim 3, wherein said surgery involves intratubal devices.

5. The method according to claim 1, wherein the image enhancing composition has a viscosity of at least 15 mPa·s.

6. The method according to claim 1, wherein the image enhancing composition has a viscosity of less than 1000 mPa·s.

7. The method according to claim 1, wherein a 1-10 ml amount of the foamed aqueous image enhancing composition is introduced into the body cavity.

8. The method according to claim 1, further comprising:
   providing an aqueous image enhancing composition, said composition consisting essentially of 1-5 wt % of cellulose and/or cellulose derivative, glycerine and a buffer, and having a viscosity between 2000-4000 mPa·sec; and
   foaming said composition with a combination of air and an aqueous solution to produce the foamed aqueous image enhancing composition, said foamed composition having a viscosity of less than 1800 mPa·sec and a pH between 5.5 and 7.

* * * * *